(12) United States Patent
Minor

(10) Patent No.: US 10,086,536 B2
(45) Date of Patent: Oct. 2, 2018

(54) METALLOGRAPHIC SAMPLE PREPARATION METHOD AND METALLOGRAPHIC SAMPLE MOLD

(71) Applicant: UNITED TECHNOLOGIES CORPORATION, Farmington, CT (US)

(72) Inventor: Michael J. Minor, Arlington, TX (US)

(73) Assignee: UNITED TECHNOLOGIES CORPORATION, Farmington, CT (US)

(*) Notice: Subject to any disclaimer, the term of this patent is extended or adjusted under 35 U.S.C. 154(b) by 257 days.

(21) Appl. No.: 14/826,598

(22) Filed: Aug. 14, 2015

(65) Prior Publication Data

US 2016/0096291 A1 Apr. 7, 2016

Related U.S. Application Data

(60) Provisional application No. 62/058,971, filed on Oct. 2, 2014.

(51) Int. Cl.
*B29C 35/08* (2006.01)
*G01N 1/36* (2006.01)
*B29C 33/38* (2006.01)
*B29C 39/10* (2006.01)
*B29K 63/00* (2006.01)
(Continued)

(52) U.S. Cl.
CPC .......... *B29C 35/0805* (2013.01); *B29C 33/38* (2013.01); *B29C 39/10* (2013.01); *G01N 1/36* (2013.01); *B29C 2035/0827* (2013.01); *B29K 2063/00* (2013.01); *B29K 2705/00* (2013.01); *B29K 2833/04* (2013.01); *B29K 2995/0027* (2013.01); *B29L 2031/40* (2013.01); *G01N 2001/364* (2013.01)

(58) Field of Classification Search
None
See application file for complete search history.

(56) References Cited

U.S. PATENT DOCUMENTS

2004/0239008 A1* 12/2004 Gottlieb .............. B29C 45/0053
264/494
2007/0160967 A1 7/2007 Halley

FOREIGN PATENT DOCUMENTS

| CN | 103543060 A | 1/2014 |
| EP | 0169298 A2 | 1/1986 |
| WO | 20090118544 A2 | 10/2009 |

OTHER PUBLICATIONS

European Search Report for Application No. 15188100.0-1553; dated Feb. 22, 2016.
(Continued)

*Primary Examiner* — Jacob T Minskey
*Assistant Examiner* — Baileigh Kate Darnell
(74) *Attorney, Agent, or Firm* — Cantor Colburn LLP

(57) ABSTRACT

The present disclosure relates generally to method for preparing metallographic samples including the steps of placing a specimen into a mold, inserting an epoxy into the mold, and exposing the mold to an ultraviolet light for a duration of time to create a mounting sample. The mold includes a peripheral wall and a bottom defining a cavity therein. The mold is formed from a material that allows ultraviolet light to penetrate the peripheral wall and bottom into the cavity. The mold includes a material operative to allow an ultraviolet light to penetrate the peripheral wall and the bottom surface into the cavity.

6 Claims, 2 Drawing Sheets

(51) Int. Cl.
B29K 705/00 (2006.01)
B29L 31/40 (2006.01)

(56) References Cited

OTHER PUBLICATIONS

English Translation of EP0169298 Abstract.
English Translation of CN103543060 Abstract.

* cited by examiner

METALLOGRAPHIC SAMPLE PREPARATION METHOD AND METALLOGRAPHIC SAMPLE MOLD

CROSS REFERENCE TO RELATED APPLICATIONS

The present application is related to, and claims the priority benefit of, U.S. Provisional Patent Application Ser. No. 62/058,971 filed Oct. 2, 2014, the contents of which are hereby incorporated in their entirety into the present disclosure.

TECHNICAL FIELD OF THE DISCLOSED EMBODIMENTS

The present disclosure is generally related to metallographic sample preparation, in particular to an improved method for preparing metallographic samples.

BACKGROUND OF THE DISCLOSED EMBODIMENTS

Metallography is the science and art of preparing a metal surface for analysis by grinding and polishing, and etching to reveal the structure of the specimen. Metallographic and materialographic specimen preparation seeks to find the true structure of the material. Mechanical preparation is the most common method of preparing the specimens for examination.

Mounting of specimens is usually necessary to allow them to be handled easily. It also minimizes the amount of damage likely to be caused to the specimen. Mounting a specimen provides a safe, standardized, and ergonomic way by which to hold a specimen during the grinding and polishing operations. Metallographic specimens are typically mounted using hot mounting or cold mounting. A typical hot mounting cycle will use hot mounting resins and a hot mounting press compressing the mounting media to 4,000 pounds per square inch (28 mega-Pascal) and heat to a temperature of 350° Fahrenheit (180° Celsius). Hot mounting samples take approximately ten minutes to process, but only one mount may be processed at a time. Additionally, hot mounting is not suitable for brittle materials (e.g. ceramics), and edge retention is problematic.

When specimens are very sensitive to pressure or temperature, cold mounts may be made with cold mounting resins. With cold mounting, specimens are placed in a mounting cup and two-part epoxy mounting material is then poured over the specimens. While multiple samples may be made at the same time with cold mounting, it generally take over an hour for the samples to cure.

Improvements in metallographic sample preparation are therefore needed in the art.

SUMMARY OF THE DISCLOSED EMBODIMENTS

In one aspect, a sample mold used in a metallographic preparation process. The mold includes a body including a peripheral wall and an adjoining bottom surface defining a cavity therein. The mold is formed from a material operative to allow an ultraviolet light to penetrate the peripheral wall and the bottom surface into the cavity. The mold includes a width dimension, and a height dimension. In one embodiment the width dimension is approximately one inch (approximately 30 millimeters) and the height dimension is approximately one half inch (approximately 15 millimeters).

In one embodiment, the material used to form the mold includes a material transparent to ultraviolet light. In one embodiment, the material is transparent to an ultraviolet light including a wavelength greater than or equal to approximately 250 nanometers. In one embodiment, the transparent material includes silicone.

In one aspect, a method for preparing a metallographic specimen is provided. The method includes the step of placing a specimen into the mold. The method proceeds to the step of inserting an epoxy into the mold. In one embodiment, a first epoxy portion may be inserted into the mold prior to placing the specimen into the mold, and a second epoxy portion may be inserted into the mold after placing the specimen into the mold. In one embodiment, the epoxy includes a low viscosity ultraviolet curable epoxy.

The method proceeds to the step of exposing the mold to an ultraviolet light for a duration of time to create a mounting sample. In one embodiment, the duration of time is less than or equal to approximately four minutes. The method further includes the step of removing the mounting sample from the mold to be analyzed.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

Other embodiments are also disclosed.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein.

DETAILED DESCRIPTION OF THE DISCLOSED EMBODIMENTS

Figure 1B:
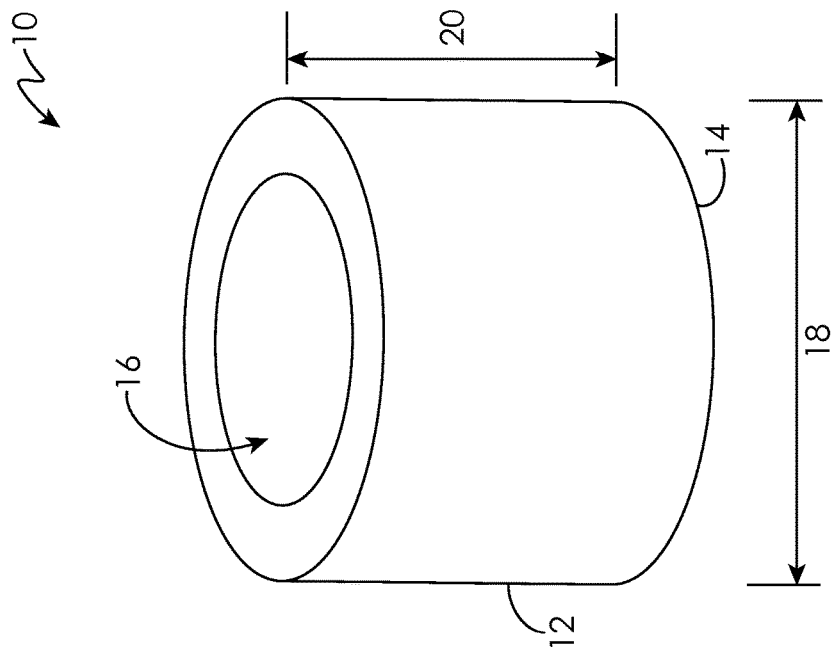
FIGS. 1A and 1B are perspective views of a mold used in a metallographic preparation process.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1A:
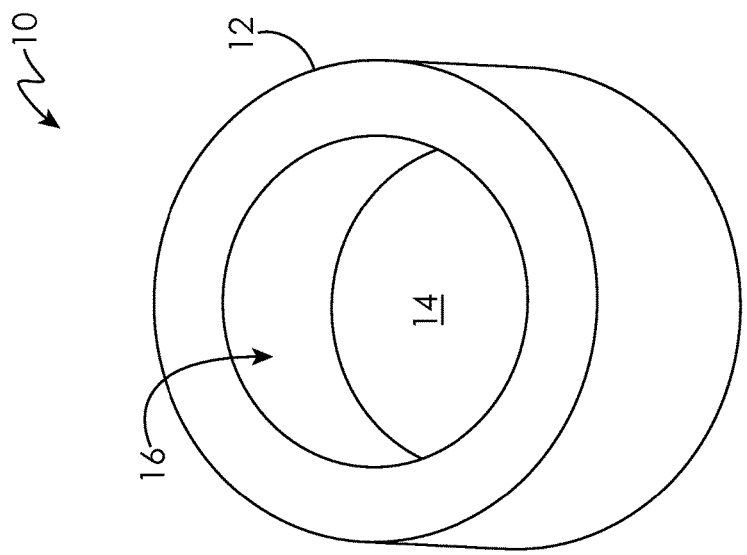

FIGS. 1A and 1B illustrate an embodiment of a sample mold, generally indicated at 10, used in a metallographic preparation process. The mold 10 is configured to house a specimen for preparation and examination. The mold 10 includes a body including a peripheral wall 12 and an adjoining bottom surface 14 defining a cavity 16 therein. The mold 10 is formed from a material operative to allow an ultraviolet light to penetrate the peripheral wall 12 and the bottom surface 14 into the cavity 16. The mold 10 includes a width dimension 18, as shown in FIG. 1B, and a height dimension 20. Although it will be appreciated that the mold 10 may include any dimension suitable for preparing a specimen, in one embodiment the width dimension 18 comprises approximately one inch (approximately 30 millimeters) and the height dimension 20 comprises approximately one half inch (approximately 15 millimeters). While the mold 10 is shown with a circular configuration, it will be appreciated that the mold 10 may be formed in any geometric shape or in a combination of different geometric shapes.

In one embodiment, the material used to form the mold 10 includes a material transparent to ultraviolet light. In one embodiment, the material is transparent to an ultraviolet light including a wavelength greater than or equal to approximately 250 nanometers (approximately $98.43 \times 10^{-7}$ inches). In one embodiment, the transparent material includes silicone. It will be appreciated that other transparent materials, such as a clear acrylic to name one non-limiting example, may also be used to form the mold 10.

Figure 2:
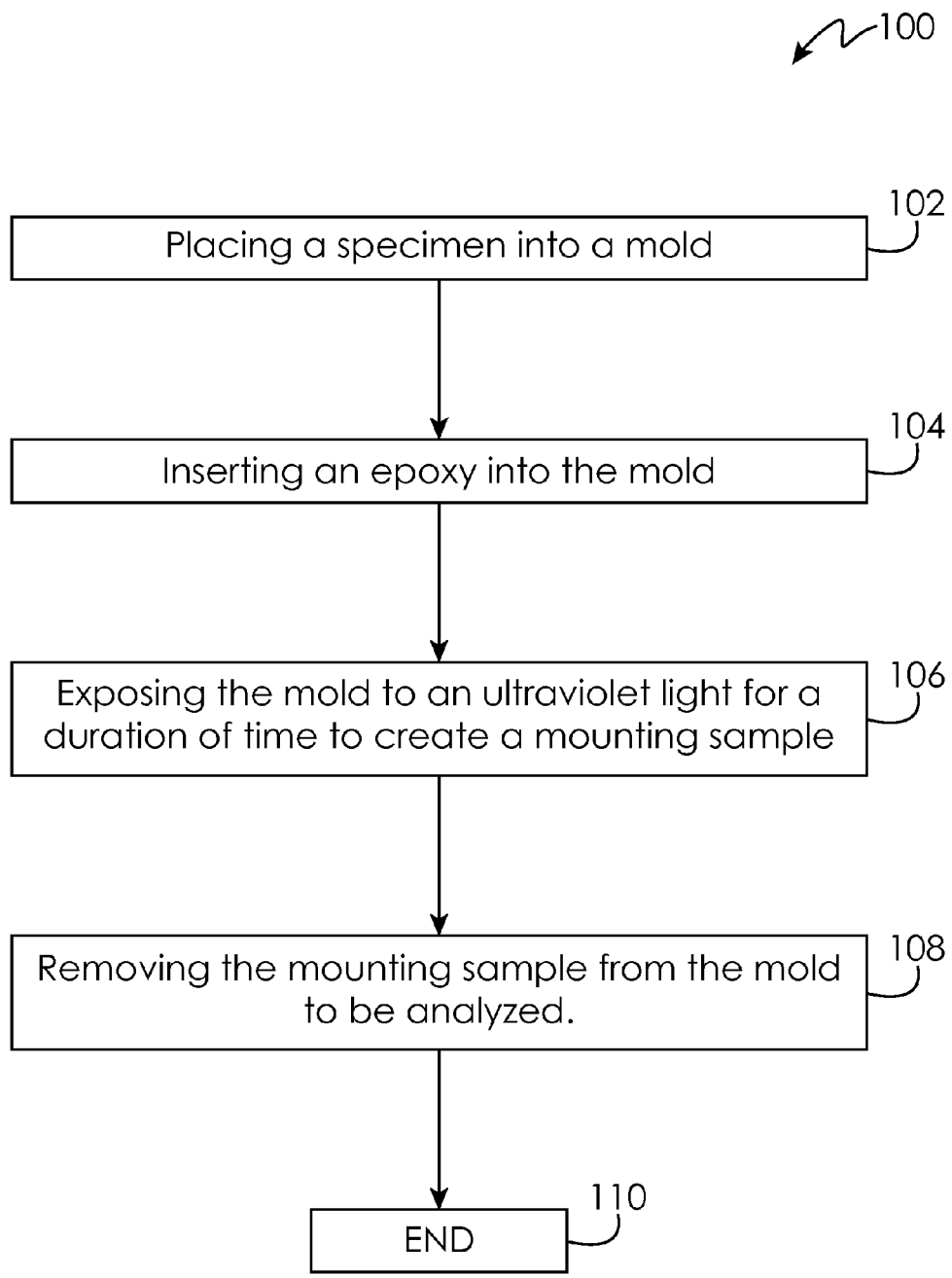
FIG. 2 is a schematic flow diagram of an embodiment of a metallographic preparation method.

FIG. 2 illustrates a method, generally indicated at 100, for preparing a metallographic specimen. The method 100 includes the step 102 of placing a specimen into the mold 10. For example, a metal specimen is placed within the cavity 16 of the mold 10 to begin preparation for examination. It will also be appreciated that materials other than metals may be placed within the cavity 16 to be prepared for examination.

The method 100 includes step 104 of inserting an epoxy into the mold 10. In one embodiment, a first epoxy portion may be inserted into the mold 10 prior to placing the specimen into the mold 10, and a second epoxy portion may be inserted into the mold 10 after placing the specimen into the mold 10. In one embodiment, the epoxy includes a low viscosity ultraviolet curable epoxy. For example, a low viscosity ultraviolet curable epoxy is inserted into the cavity 16 along with the specimen, either before the specimen is inserted, after the specimen is inserted, or a combination of before the specimen is inserted and after the specimen is inserted.

The method includes step 106 of exposing the mold 10 to an ultraviolet light for a duration of time to create a mounting sample. Exposing the mounting sample to the ultraviolet light cures the epoxy within the cavity to allow for future examination. It will be appreciated that the mounting sample may be exposed to ultraviolet light from any direction. In one embodiment, the duration of time is less than or equal to approximately four minutes. It will be appreciated that the duration of time may be greater than four minutes. The duration of time to expose the mounting sample to ultraviolet light is dependent, in part, upon the size of the mounting sample (i.e. the depth of penetration of the ultraviolet light). For example, every one half inch of required penetration of ultraviolet light may equate to approximately five minutes of curing time.

The method further includes step 108 of removing the mounting sample from the mold 10 to be analyzed. For example, after the epoxy has cured from exposure to the ultraviolet light, the mounting sample may be removed from the mold 10 for examining the specimen surface and handling the specimen during further processing of the specimen, such as by cutting and/or polishing, to name just two non-limiting examples.

It will be appreciated that as the method 100 includes the step of exposing the mounting sample to an ultraviolet light for a duration of time. Curing the mounting sample under ultraviolet light significantly reduces the time required to prepare a sample compared to a cold mounting process, and allows for the creation of a greater quantity of samples compared to a hot mounting process. It will also be appreciated that the mold 10 is formed from a material configured to allow ultraviolet light to penetrate the peripheral walls 12 and bottom 14 into the cavity 16 to aid in curing the epoxy in a shorter amount of time.

While the invention has been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method for preparing a metallographic sample, the method comprising the steps:
    a) placing a metallographic sample into a mold, the mold having a peripheral wall and a bottom surface forming a cavity, wherein the mold comprises a material transparent to ultraviolet light and is selected from a group of materials consisting of silicone and clear acrylic;
    b) inserting an epoxy into the mold, the epoxy being curable when exposed to ultraviolet light; and
    c) curing the epoxy within the mold by a curing process consisting of exposing the epoxy to ultraviolet light for a duration of time to create a mounted metallographic sample, wherein the step of curing the epoxy excludes cold mounting and/or hot mounting of the metallographic sample.

2. The method of claim 1, wherein step (b) comprises inserting a first epoxy portion into the mold prior to step (a) and a second epoxy portion into the mold after step (a).

3. The method of claim 1, further comprising removing the mounted metallographic sample from the mold.

4. The method of claim 1, wherein the mold comprises a material that is transparent to an ultraviolet light comprising a wavelength greater than or equal to approximately 250 nanometers.

5. The method of claim 1, wherein the duration of time is less than or equal to approximately four minutes.

6. A metallographic sample made by the method of claim 1.

* * * * *